United States Patent [19]

Hauser

[11] Patent Number: 4,619,794
[45] Date of Patent: Oct. 28, 1986

[54] SPONTANEOUS PREPARATION OF SMALL UNILAMELLAR LIPOSOMES

[75] Inventor: Helmut Hauser, Uerikon, Switzerland

[73] Assignee: Ciba-Geigy Corporation, Ardsley, N.Y.

[21] Appl. No.: 696,228

[22] Filed: Jan. 29, 1985

Related U.S. Application Data

[63] Continuation of Ser. No. 466,235, Feb. 14, 1983, abandoned.

[30] Foreign Application Priority Data

Feb. 17, 1982 [CH] Switzerland ............................ 981/82
Jan. 17, 1983 [CH] Switzerland ............................ 237/83

[51] Int. Cl.⁴ ............................................. B01J 13/02
[52] U.S. Cl. ...................................... 264/4.1; 264/4.3; 424/38; 428/402.2; 436/829
[58] Field of Search ....................... 264/4.1; 428/402.2; 424/38; 436/829

[56] References Cited

U.S. PATENT DOCUMENTS 4,145,410 3/1979 Sears ............................ 428/402.2 X
4,224,179 9/1980 Schneider .................... 428/402.2 X
4,342,826 8/1982 Cole ................................ 436/829 X
4,356,167 10/1982 Kelly ..................................... 424/38

FOREIGN PATENT DOCUMENTS 0036676 9/1981 European Pat. Off. .

OTHER PUBLICATIONS

H. E. Schaeffer et al.: "Liposomes in Topical Drug Delivery", Invest. Opthal. Mol. Vis. Sci., 21, 220–227 (1982).

Primary Examiner—Richard D. Lovering
Attorney, Agent, or Firm—Michael W. Glynn; Irving M. Fishman

[57] ABSTRACT

The present invention relates to a novel advantageous process for the preparation of unilamellar liposomes in aqueous phase by converting a suitable lipid component, e.g. phosphatidic acid, into the ionic form by subjecting the lipid dispersion to a change in pH value and subsequently neutralizing it. Formation of the unilamellar liposomes is spontaneous, i.e. it takes place without additional external supply of energy. The liposomes obtainable by the process of this invention can be used therapeutically as carriers for drugs of the most widely different kind.

24 Claims, No Drawings

SPONTANEOUS PREPARATION OF SMALL UNILAMELLAR LIPOSOMES

This is a continuation of application Ser. No. 466,235 filed on Feb. 14, 1983 now abandoned.

The present invention relates to a process for the preparation of unilamellar liposomes in aqueous phase.

Liposomes have been described in the literature in a wide range of publications, and many investigations are concerned with their structure and use. A distinction is made between unilamellar liposomes having a double layer of lipids and multilamellar liposomes having a number of double layers of lipids of onion-like structure.

Unilamellar liposomers have a spherical shell and e.g. a diameter of about 200 to 50,000 Å, preferably of about 200 to 30,000 Å. The spherical shell consists of a double layer of the lipid components, e.g. amphiphatic lipids such as phospholipids, e.g. phosphatidic acid, lecithin or cephalin, with or without neutral lipids, e.g. cholesterol. This double layer surrounds a cavity which contains an aqueous phase. Unilamellar liposomes are also known as vesicles.

There is great interest in the therapeutic use of liposomes as carriers for a very wide range of active ingredients. Accordingly, liposomes have been proposed as carriers for proteins, e.g. antibodies or enzymes, hormones, vitamins or genes or, for analytical purposes, as carriers for marker compounds. For example, U.S. Pat. No. 3 993 754 describes a chemotherapeutic process for treating tumour cells, wherein liposomes are used as drug carriers.

The drug is encapsulated either during the formation of the liposomes or subsequently by diffusion. The preparation of liposomes and the encapsulation of the drug can be effected by different methods, a survey of which may be found in the article "Liposomes—Problems and promise as selective drug carriers" by Stanley B. Kaye, Cancer Treatment Reviews (1981), 8, pp. 27–50. Further methods of preparing liposomes for encapsulating drugs are also described by Barenholz et al. in Biochemistry, Vol. 16, No. 12, 2806–2810, and also in German Offenlegungsschrift specifications No. 28 19 855, 29 02 672, 25 32 317 and 28 42 608, in U.S. Pat. No. 4 053 585, and in European patent application No. 36 676.

The lipid components, e.g. phospholipids such as phosphatidic acid, lecithin or cephalin, with or without neutral lipids, e.g. cholesterol, are dissolved in an organic solvent, e.g. chloroform or benzene. After stripping off the solvent, there remains a homogeneous layer, e.g. a film, of the particular lipid components. The lipid components are subsequently dispersed in an aqueous phase which contains the drug, e.g. by shaking. In the subsequent ultrasonic irradiation there are formed unilamellar liposomes which encapsulate the drug.

In many prior art methods there are obtained aqueous phases with mixtures of both unilamellar and multilamellar liposomes whose structure and size are random, can scarcely be influenced, and may vary considerably. Aqueous phases containing a high concentration of unilamellar liposomes are so far only obtainable by methods employing complicated apparatus, e.g. by ultrasonication, dialysis or gel filtration.

In the process of this invention it is possible to prepare, in simple manner, aqueous phases having a high to almost quantitative content of unilamellar liposomes, which aqueous phases can contain small unilamellar liposomes (SUL) with a diameter of about 200 to 600 Å, and large unilamellar liposomes (LUL) with a diameter of about 600 to 3000 Å. A particular advantage of the process of the present invention consists in the fact that SUL and LUL of relatively uniform size are obtained and that the ratio of SUL to LUL in the disperse phase may vary. Small unilamellar liposomes can be separated from large unilamellar liposomes by means of suitable separating methods, e.g. by gel filtration or in an ultrafiltration cell.

Accordingly, the present invention provides a process for the preparation of unilamellar liposomes, which comprises (a) dispersing a lipid of the formula

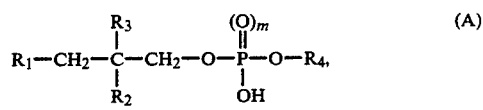

wherein m is 0 or 1, one of $R_1$ and $R_2$ is hydrogen, hydroxy or $C_1$–$C_4$ alkyl, and the other is alkyl, alkenyl, alkoxy or alkenyloxy, each of 10 to 20 carbon atoms, or is acyloxy of 10 to 50 atoms, $R_3$ is hydrogen or $C_1$–$C_4$alkyl, and $R_4$ is hydrogen, $C_1$–$C_7$ alkyl, a carbohydrate radical of 5 to 12 carbon atoms or, if $R_1$ and $R_2$ are hydrogen or hydroxy and $R_3$ is hydrogen, is a steroid radical, and a suitable additional lipid and/or a fatty acid and a suitable additional lipid with the exception of a sterol; or a lipid of the formula A, wherein m is 0 or 1, each of $R_1$ and $R_2$ independently of the other is alkyl, alkenyl, alkoxy or alkenyloxy, each of 10 to 20 carbon atoms, or is acyloxy of 10 to 50 atoms, $R_3$ and $R_4$ are hydrogen, and optionally a suitable additional lipid, in an aqueous phase having a pH value higher than 7; or (b) dispersing a lipid of the formula A, wherein m is 0 or 1, one of $R_1$ and $R_2$ is hydrogen, hydroxy or lower Cl-C4-alkyl, and the other is alkyl, alkenyl, alkoxy or alkenyloxy, each of 10 to 20 carbon atoms, or is acyloxy of 10 to 50 carbon atoms, $R_3$ is hydrogen, and $R_4$ is lower alkyl which is substituted by an ammonio group, and optionally a suitable additional lipid; or a lipid of the formula A, wherein m is 0 or 1, each or $R_1$ and $R_2$ independently of the other is alkyl, alkenyl or alkenyloxy, each of 10 to 20 carbon atoms, or is acyloxy of 10 to 50 carbon atoms, $R_3$ is hydrogen, and $R_4$ is lower alkyl which is substituted by an ammonio-lower alkylammonio group, and a suitable additional lipid, in an aqueous phase having a pH value lower than 7, and, if necessary, neutralising the aqueous phase and, if desired, enriching and/or separating the unilamellar liposomes so obtained.

Throughout this specification, the general terms employed have preferably the following meanings:

In process (a):

$R_1$ $R_2$ or $R_3$ as lower $C_1$–$C_4$alkyl is e.g. preferably methyl, and also ethyl, n-propyl or n-butyl.

$R_1$ or $R_2$ as alkyl is preferably n-decyl, n-undecyl, n-dodecyl (lauryl), n-tridecyl, n-tetradecyl (myristyl), n-pentadecyl, n-hexadecyl (cetyl), n-octadecyl (stearyl) or n-eicosyl (arachinyl), and also n-heptadecyl or n-nonadecyl. $R_1$ or $R_2$ as alkenyl is preferably 9-cis-dodecenyl (lauroleyl), 9-cis-tetradecenyl (myristoleyl), 9-cis-hexadecenyl (palmitoleinyl), 6-cis-octadecenyl (petroselinyl), 6-trans-octadecenyl (petroselaidinyl), 9-cis-octadecenyl (oleyl), 9-trans-octadecenyl (elaidinyl) or 9-cis-eicosenyl (gadoleinyl), and also 1-decenyl, 1-undecenyl, 1-dodecenyl, 1-tridecenyl, 1-tetradecenyl, 1-pentadecenyl, 1-hexadecenyl, 1-heptadecenyl, 1-octadecenyl, 9-cis-12-trans-octadecadienyl (linolyl), 9-trans-12-trans-octadecadienyl (linolaidinyl), 9-cis-12-cis-octadienyl (linoleyl), 9-cis-11-trans-13-trans-octadecatrienyl (β-eleostearinyl), 9-cis-12-cis-15-cis-octadecatrienyl (linolenyl), 9-, 11-, 13-15-octadecatetraenyl (parinaryl), 1-nonadecenyl, 1-eicosenyl, 5-, 11-, 14-eicosatrienyl or 5-, 8-, 11-, 14-eicosatetraenyl (arachidonyl).

$R_1$ or $R_2$ as alkoxy is preferably n-decyloxy, n-dodecyloxy (lauryloxy), n-tetradecyloxy (myristyloxy), n-hexadecyloxy (cetyloxy), n-octadecyloxy (stearyloxy) or n-eicosyloxy (arachinyloxy), and also n-undecyloxy, n-tridecyloxy, n-pentadecyloxy, n-heptadecyloxy or n-nonadecyloxy.

$R_1$ or $R_2$ as alkenyloxy are preferably 9-cis-dodecenyloxy (lauroleyloxy), 9-cis-tetradecenyloxy (myristoleyloxy), 9-cis-hexadecenyloxy (palmitoleinyloxy), 6-cis-octadecenyloxy (petroselinyloxy), 6-trans-octadecenyloxy (petroselaidinyloxy), 9-cis-octadecenyloxy (oleyloxy), 9-trans-octadecenyloxy (elaidinyloxy) or 9-cis-eicosenyl (gadeleinyloxy) and also 1-decenyloxy, 1-undecenyloxy, 1-dodecenyloxy, 1-tridecenyloxy, 1-tetradecenyloxy, 1-pentadecenyloxy, 1-hexadecenyloxy, 1-heptadecenyloxy, 1-octadecenyloxy, 9-cis-12-trans-octadecadienyloxy (linolyloxy), 9-trans-12-trans-octadecadienyloxy (linolaidinyloxy), 9-cis-12-cis-octadienyloxy (linoleyloxy), 9-cis-11-trans-13-trans-octadecatrienyloxy (β-eleostearinyloxy), 9-cis-12-cis-15-cis-octadecatrienyloxy (linolenyloxy), 9-, 11-, 13-, 15-octadecatetraenyloxy (parinaryloxy), 1-nonadecenyloxy, 1-eicosenyloxy, 5-, 11-, 14-eicosatrienyloxy or 5-, 8-, 11-, 35 14-eicosatetraenyloxy (arachidonyloxy).

$R_1$ or $R_2$ as acyloxy of 10 to 50 carbon atoms is e.g. alkanoyloxy, alkanoyloxy substituted by an aromatic ring system, or alkenoyloxy.

$R_1$ or $R_2$ as alkanoyloxy is preferably n-decanoyloxy, n-dodecanoyloxy (lauroyloxy), n-tetradecanoyloxy (myristoyloxy), n-hexadecanoyloxy, n-hexadecanoyloxy (palmitoyloxy), n-octadecanoyloxy (stearoyloxy) or n-eicosoyloxy (arachinoyloxy), and also n-undecanoyloxy, n-tridecanoyloxy, n-pentadecanoyloxy, n-heptadecanoyloxy or n-nonadecanoyloxy.

$R_1$ or $R_2$ as alkanoyloxy substituted by an aromatic ring system is e.g. phenyl-n-alkanoyloxy, wherein the phenyl moiety is in the ω-position of the alkanoyloxy moiety, e.g. phenyl-n-butyryloxy, phenyl-n-pentanoyloxy, phenyl-n-hexanoyloxy, phenyl-n-heptanoyloxy, phenyl-n-octanoyloxy, phenyl-n-nonanoyloxy, phenyl-n-decanoyloxy, phenyl-n-undecanoyloxy or phenyl-n-dodecanoyloxy, 3- or 4-, preferably 4-alkylphenyl-n-alkanoyloxy, wherein the alkylphenyl moiety is in the ω-position of the alkanoyloxy radical, e.g. 4-n-butyl-, 4-n-pentyl-, 4-n-hexyl-, 4-n-octyl-, 4-n-decyl- or 4-n-dodecylphenyl-n-butyryloxy, -n-pentanoyloxy-, n-hexanoyloxy, -n-octanoyloxy, -n-decanoyloxy or -n-dodecanoyloxy, pyren-1-yl-n-alkanoyloxy, wherein the pyrene moiety is in the ω-position of the alkanoyloxy radical, e.g. pyren-1-yl-n-butyryloxy, pyren-1-yl-n-pentanoyloxy, pyren-1-yl-n-hexanoyloxy, pyren-1-yl-n-octanoyloxy, pyren-1-yl-n-decanoyloxy or pyren-1-yl-decanoyloxy, or 6- or 8-alkylpyren-1-yl-n-alkanoyloxy, wherein the alkylpyren-1-yl moiety is in the ω-position of the alkanoyl radical, e.g. 6- or 8-lower alkylpyren-1-yl-n-butyryloxy, e.g. 6- or 8-ethylpyren-1-yl-n-butyryloxy, -n-pentanoyloxy, -n-hexanoyloxy, -n-octanoyloxy, -n-decanoyloxy or -n-decanoyloxy, or 6- or 8-n-butylpyren-1-yl-n-butyryloxy, -n-pentanoyloxy, -n-hexanoyloxy, -n-octanoyloxy, -n-decanoyloxy or -n-dodecanoyloxy, or 6- or 8-alkylpyren-1-yl-n-alkanoyloxy, e.g. 6- or 8-n-decyl-, -n-dodecyl-, -n-tetradecyl-, -n-hexadecyl- or 6- or 8-n-octadecylpyren-1-yl-n-butyryloxy, -n-pentanoyloxy, n-hexanoyloxy, n-octanoyloxy, -n-decanoyloxy or -n-dodecanoyloxy.

$R_1$ or $R_2$ as alkanoyloxy substituted by an aromatic ring system is preferably 4-(4-n-decylphenyl)decanoyl, 4-(pyren-1-yl)-butanoyl, 6-(pyren-1-yl)hexanoyl, 8-(pyren-1-yl)octanoyl, 10-(pyren-1-yl)octanoyl, 6-(6- or 8-ethylpyren-1-yl)octanoyl, 6-(6- or 8-n-butylpyren-1-yl)hexanoyl and 10-(6- or 8-n-octadecylpyren-1-yl)decanoyl.

$R_1$ or $R_2$ as alkenoyloxy is preferably 9-cis-dodecenoyloxy (lauroleoyloxy), 9-cis-tetradecenoyloxy (myristoleoyloxy), 9-cis-hexadecenoyloxy (palmitoleinoyloxy), 6-cis-octadecenoyloxy (petroselinoyloxy), 6-trans-octadecenoyloxy (petroselaidinoyloxy), 9-cis-octadecenoyloxy (oleoyloxy), 9-trans-octadecenoyloxy (elaidinoyloxy) or 9-cis-eicosenoyl (gadoleinoyloxy), and also 9-cis-12-trans-octadienoyloxy (linoloyl), 9-trans-12-trans-octadecadienoyloxy (linolaidinoyloxy), 9-cis-12-cis-octadienoyloxy (linoleoyloxy), 9-cis-11-trans-13-trans-octadecatrienoyloxy (linoleoyloxy), (linolenoyloxy), 9-, 11-, 13-, 15-octadecatetraenoyloxy (parinaroyloxy), 5-, 11-, 14-eicosatrienoyloxy or 5-, 8-, 11-, 14-eicosatetraenoyloxy (arachidonoyloxy).

$R_4$ as $C_1$–$C_7$alkyl is e.g. methyl, ethyl, isopropyl, n-propyl, isobutyl or n-butyl, and may be substituted by acid groups, e.g. carboxyl or sulfo, by basic groups, e.g. amino, lower alkylamino, e.g. methylamino or ethylamino, di-lower alkylamino, e.g. dimethylamino or diethylamino, by acid and basic groups, e.g. carboxyl and amino, in which case the amino group is in α-position to the carboxyl group, a tri-lower alkylammonio group, e.g. trimethylammonio or triethylammonio, by free or etherified hydroxyl groups, where two etherified hydroxyl groups may be linked to each other through a divalent hydrocarbon radical, e.g. by methylene, ethylene, ethylidene, 1,2-propylene or 2,2-propylene, by halogen, e.g. chlorine or bromine, by lower alkoxycarbonyl, e.g. methoxycarbonyl or ethoxycarbonyl, or by lower alkanesulfonyl, e.g. methanesulfonyl.

$R_4$ as substituted $C_1$–$C_7$ alkyl is preferably carboxy-lower alkyl, e.g. carboxymethyl, 2-carboxyethyl or 3-carboxy-n-propyl, amino-lower alkyl, e.g. aminomethyl, 2-aminoethyl or 3-amino-n-propyl, lower alkylamino-lower alkyl, e.g. methylaminomethyl or ethylaminomethyl, 2-methylaminoethyl or 3-methylamino-n-propyl, di-lower alkylamino-lower alkyl, e.g. dimethylaminomethyl or diethylaminomethyl, 2-dimethylaminoethyl or 3-dimethylamino-n-propyl, ω-amino-ω-carboxy-lower alkyl, e.g. 2-amino-2-carboxyethyl or 3-amino-3-carboxy-n-propyl, tri-lower alkylammonio-lower alkyl, e.g. 2-trimethylammonioethyl or 2-triethylammonioethyl, or 3-trimethylammonio-n-propyl or 3-triethylammonio-n-propyl, hydroxy-lower alkyl, e.g. 2-hydroxyethyl or 2,3-dihydroxypropyl, lower alkoxy-lower alkyl, e.g. methoxymethyl or ethoxymethyl, 2-methoxyethyl or 3-methoxy-n-propyl, lower alkylenedioxy-lower alkyl, e.g. 2,3-ethylenedioxypropyl or 2,3-(2,2-propylene)dioxypropyl, or halo-lower alkyl, e.g. chloromethyl or bromomethyl, 2-chloroethyl or 2-bromoethyl, 2- or 3-chloro-n-propyl or 2- or 3-bromo-n-propyl.

$R_4$ as a carbohydrate radical of 5 to 12 carbon atoms is e.g. a natural monosaccharide radical which is derived from a pentose or hexose in the form of an aldose or a ketose.

A pentose in the form of an aldose is e.g. D-ribose, D-arabinose, D-xylose or D-lyxose. A pentose in the form of a ketose is e.g. D-ribulose or D-xylulose. A hexose in the form of an aldose is e.g. D-allose, D-altrose, D-glucose, D-mannose, D-galactose or D-talose. A hexose in the form of a ketose is e.g. D-psicose, D-fructose, D-sorbose or D-tagatose.

A hexose is preferably in cyclic form, e.g. in the form of a pyranose (aldose), e.g. $\alpha$- or $\beta$-D-glucopyranose, or a furanose, e.g. $\alpha$- or $\beta$-D-fructofuranose. The pyranosyl radical is preferably esterified with the phosphatidyl group through the hydroxy group in the 1- or 6-position, and the furanosyl radical is esterified with the phosphatidyl group through the hydroxyl group in the 1- or 5-position.

A carbohydrate radical $R_4$ of 5 to 12 carbon atoms is also a natural disaccharide radical, e.g. a disaccharide radical which is formed from two hexoses by condensation of two aldoses, e.g. D-glucose or D-galactose or an aldose, e.g. D-glucose, with a ketose, e.g. fructose.

Disaccharides formed from two aldoses, e.g. lactose or maltose, are preferably esterified with the phosphatidyl group through the hydroxyl group which is in the 6-position of the particular pyranosyl radical. Disaccharides formed from an aldose and a ketose, e.g. saccharose, are preferably esterified with the phosphatidyl group through the hydroxyl group which is in the 6-position of the pyranosyl radical or in the 1-position of the furanosyl radical.

A carbohydrate radical $R_4$ of 5 to 12 carbon atoms is further a derived mono- or disaccharide radical, wherein e.g. the aldehyde group and/or one or two hydroxyl end groups are oxidised to carboxyl groups, and is e.g. a D-gluconic, D-glucaric or D-glucoronic acid radical which is preferably in the form of a cyclic lactone radical. Likewise, the aldehyde or keto group of a derived mono or disaccharide radical can be reduced to hydroxyl groups, e.g. inositol, sorbitol or D-mannitol, or hydroxyl groups can be replaced by hydrogen, e.g. desoxy sugar, e.g. 2-desoxy-D-ribose, L-rhamnose or L-fucose, or by amino groups, e.g. amino sugar, e.g. D-glucosamine or D-galactosamine.

A carbohydrate radical $R_4$ can also be a fission product formed by reacting one of the mono- or disaccharides mentioned above with a strong oxidising agent, e.g. periodic acid.

A steroid radical $R_4$ is e.g. a sterol radical which is esterified with the phosphatidyl group through the hydroxyl group which is in the 3-position of the steroid skeleton.

A sterol radical is e.g. lanosterol, sitosterol, coprostanol, cholestanol, glycocholic acid, ergosterol or stigmasterol, but is preferably cholesterol.

If $R_4$ is a steroid radical, $R_1$ and $R_2$ are preferably hydroxyl and $R_3$ is hydrogen.

A fatty acid is e.g. a saturated or an unsaturated aliphatic carboxylic acid of 4 to 26, preferably of 10 to 20, carbon atoms.

A saturated aliphatic carboxylic acid is e.g. a straight chain aliphatic carboxylic acid of 10 to 20 carbon atoms, e.g. capric acid ($C_{10}$), undecanoic acid ($C_{11}$), lauric acid ($C_{12}$), tridecanoic acid ($C_{13}$), myristic acid ($C_{14}$), pentadecanoic acid ($C_{15}$), palmitic acid ($C_{16}$), margaric acid ($C_{17}$), stearic ($C_{18}$), nonadecanoic acid ($C_{19}$) or arachinic acid ($C_{20}$).

A saturated aliphatic carboxylic acid is e.g. a branched chain aliphatic acid of 10 to 20 carbon atoms, e.g. isomyristic acid ($C_{14}$), isopalmitic acid ($C_{16}$) or isostearic acid ($C_{18}$).

An unsaturated aliphatic carboxylic acid of 10 to 20 carbon atoms has e.g. an even number of carbon atoms and up to five double bonds and is e.g. myristoleic acid ($C_{14}$), palmitoleic acid ($C_{16}$), palmitaleidic acid ($C_{18}$), petroselinic acid ($C_{16}$), oleic acid acid ($C_{18}$), elaidic acid ($C_{18}$), vaccenic acid ($C_{18}$), linolic acid ($C_{18}$), linolelaidic acid ($C_{18}$), linolenic acid ($C_{18}$), cis-eicos-5-enoic acid ($C_{20}$), cis-11-eicosenoic acid, 11,14-eicosadienoic acid, 11-, 14- and 17-eicosatrienoic acid, arachidonic acid or 5-, 8-, 11-, 14- and 17-eicosapentenoic acid.

The fatty acid may be in undissociated form or in the form of a salt, e.g. an alkali metal salt such as the sodium or potassium salt.

A suitable additional lipid is e.g. a lipid of the formula A, wherein m is 0 or 1, each of $R_1$ and $R_2$ independently of the other is alkyl, alkenyl, alkoxy or alkenyloxy, each of 10 to 20 carbon atoms, or is acyloxy of 10 to 50 carbon atoms, $R_3$ is hydrogen, and $R_4$ is hydrogen or $C_1$–$C_7$alkyl, a carbohydrate radical of 5 to 12 carbon atoms or a steroid radical.

$R_1$, $R_2$ and $R_3$ have the meanings assigned to them above. $R_4$ is additionally lower alkyl substituted by tri-lower alkylammonio e.g. trimethylammonio and is e.g. 2-trimethylammoniomethyl (cholinyl).

A suitable additional lipid is preferably a lipid of the formula A, wherein $R_1$ and $R_2$ are acyloxy, $R_3$ is hydrogen and $R_4$ is 2-trimethylammonioethyl or 2-aminoethyl. Such an additional lipid is e.g. a natural lecithin, e.g. egg lecithin or lecithin from soybeans, if $R_4$ is 2-trimethylammonioethyl, and a natural cephalin, e.g. egg cephalin or cephalin from soybeans, if $R_4$ is 2-aminoethyl.

Further preferred additional lipids are synthetic lecithins ($R_4$=2-trimethylammonioethyl) and synthetic cephalins ($R_4$=2-aminoethyl) of the formula A, wherein $R_1$ and $R_2$ are identical acyloxy radicals such as lauryloxy, oleoyloxy, linoyloxy, linoleoyloxy or arachinoyloxy, e.g. dilauroyl lecithin or cephalin, dimyristoyl lecithin or cephalin, dipalmitoyl lecithin or cephalin, distearoyl lecithin or cephalin, diarachinoyl lecithin or cephalin, dioleoyl lecithin or cephalin, dilinoyl lecithin or cephalin, dilinoleoyl lecithin or cephalin, or diarachinoyl lecithin or cephalin, $R_1$ and $R_2$ are different acyloxy radicals, e.g. $R_1$ is palmitoyloxy and $R_2$ is oleoyloxy, e.g. 1-palmitoyl-2-oleoyl lecithin or cephalin, $R_1$ and $R_2$ are identical alkoxy radicals, e.g. tetradecyloxy or hexadecyloxy, e.g. ditetradecyl lecithin or cephalin, or dihexadecyl lecithin or cephalin, $R_1$ is alkenyl and $R_2$ is acyloxy, e.g. a plasmalogen ($R_4$=trimethylammonioethyl), or $R_1$ is acyloxy, e.g. myristoyloxy or palmitoyloxy, and $R_2$ is hydroxy, e.g. a natural or synthetic lysolecithin or lysocephalin, e.g. 1-myristoyl lysolecithin or lysocephalin or 1-palmitoyl lysolecithin or lysocephalin, and $R_3$ is hydrogen.

A suitable additional lipid is also a lipid of the formula A, wherein m is 1, $R_1$ is alkenyl, $R_2$ is acylamido, $R_3$ is hydrogen, and $R_4$ is a 2-trimethylammonioethyl radical (choline radical). Such a lipid is known as sphingomyelin.

A suitable additional lipid is furthermore a lysolecithin analogue, e.g. 1-lauroyl-1,3-propanediol-3-phosphorylcholine, a monoglyceride, e.g. monoolein or monomyristin, a cerebroside, a ganglioside or a glyceride which contains no free or etherified phosphoryl or phosphonyl groups in the 3-position. Such a glyceride is e.g. a diacylglyceride or 1-alkenyl-1-hydroxy-2-acylglyceride containing the indicated acyl and alkenyl groups, wherein the 3-hydroxy group is etherified by one of the indicated carbohydrate radicals, e.g. a galactosyl radical, e.g. a monogalactosyl glycerol.

Yet another additional lipid is a neutral lipid which is contained in cell membranes and is soluble only in apolar organic solvents, e.g. in chloroform. Examples of neutral lipids are steroids such as oestradiol or sterol, e.g. cholesterol, $\beta$-sitosterol, desmosterol, 7-ketocholesterol or $\beta$-cholestanol, fat-soluble vitamins such as vitamin A, e.g. vitamin $A_1$ or $A_2$, vitamin E, vitamin K such as vitamin $K_1$ or $K_2$, vitamin $D_2$ or $D_3$, or any protein.

The aqueous dispersion preferably contains a lipid of the formula A, wherein m is 0, $R_1$ is alkyl, e.g. n-dodecyl (lauryl), n-tridecyl, n-tetradecyl (myristyl), n-pentadecyl, n-hexadecyl (cetyl), n-heptadecyl or n-octadecyl (stearyl), alkoxy, e.g. n-dodecyloxy (lauryloxy), n-tetradecyloxy (myristyloxy), n-hexadecyloxy (cetyloxy), or n-octadecyloxy (stearyloxy), acyloxy, e.g. lauroyloxy, myristoyloxy, palmitoyloxy or stearyloxy, $R_2$ is hydrogen or hydroxy, $R_3$ is hydrogen or lower alkyl, e.g. methyl, and $R_4$ is hydrogen, lower alkyl, e.g. methyl or ethyl, lower alkyl substituted by acid and basic groups, e.g. carboxy and amino, e.g. $\omega$-amino-$\omega$-carboxy-lower alkyl, e.g. 2-amino-2-carboxyethyl or 3-amino-3-carboxy-n-propyl, hydroxy-lower alkyl, e.g. 2-hydroxyethyl or 2,3-hydroxypropyl, lower alkylenedioxy-lower alkyl, e.g. 2,3-ethylenedioxypropyl or 2,3-(2,2-propylene)dioxypropyl, halo-lower alkyl, e.g. 2-chloroethyl or 2-bromoethyl, a carbohydrate radical of 5 to 12 carbon atoms, e.g. inositol, or a steroid radical, e.g. a sterol, e.g. cholesterol; and an additional lipid of the formula A, wherein $R_1$ and $R_2$ are acyloxy, e.g. lauroyloxy, myristoyloxy, palmitoyloxy or stearoyloxy, $R_3$ is hydrogen and $R_4$ is 2-trimethylammonioethyl or 2-aminoethyl. The aqueous dispersion may also preferably contain a lipid of the formula A, wherein $R_1$ and $R_2$ are acyloxy, e.g. lauroyloxy, myristoyloxy, palmitoyloxy or stearoyloxy, $R_3$ is hydrogen and $R_4$ is hydrogen, and optionally an additional lipid of the formula A, wherein $R_1$ and $R_2$ are acyloxy, e.g. lauroyloxy, myristoyloxy, palmitoyloxy or stearoyloxy, $R_3$ is hydrogen and $R_4$ is 2-trimethylammonioethyl, 2-aminoethyl, lower alkyl substituted by acid and basic groups such as carboxyl and amino, e.g. $\omega$-amino-$\omega$-carboxy-lower alkyl, e.g. 2-amino-2-carboxyethyl or 3amino-3-carboxy-n-propyl, or a carbohydrate radical of 5 to 12 carbon atoms, e.g. inositol or a monoglyceride, e.g. monoolein or monomyristin, or a sterol, e.g. cholesterol.

The aqueous dispersion contains in particular a lysophosphatidic acid, e.g. a natural lysophosphatidic acid such as egg lysophosphatidic acid, or a synthetic lysophosphatidic acid, e.g. 1-lauroyl-lysophosphatidic acid, 1-myristoyl-lysophosphatidic acid or 1-palmitoyl-lysophosphatidic acid, a beef brain lysophosphatidylserine, or a synthetic lysophosphatidylserine, e.g. 1-myristoyllysophosphatidylserine or 1-palmitoyl-lysophosphatidylserine, a lysophosphatidyl glycerol or a lysophosphatidylinositol, and additionally a lecithin such as a natural lecithin, e.g. egg lecithin, or a lecithin containing identical acyloxy groups, e.g. dimyristoyl lecithin or dipalmitoyl lecithin, a lecithin containing different acyloxy groups, e.g. 1-palmitoyl-2-oleoyl lecithin, or additionally a cephalin, e.g. a natural cephalin such as egg cephalin, or a cephalin containing different acyloxy groups, e.g. 1-palmitoyl-2-oleoylcephalin.

The aqueous dispersion may also contain in particular a natural phosphatidic acid, e.g. egg phosphatidic acid, a synthetic phosphatidic acid, e.g. dilauroylphosphatidic acid, dimyristoylphosphatidic acid, dipalmitoylphosphatidic acid or 1-palmitoyl-2-oleoylphosphatidic acid, and optionally additionally a lecithin, e.g. a natural lecithin such as egg lecithin, a lecithin containing identical acyloxy groups, e.g. dimyristoyl lecithin or dipalmitoyl lecithin, or a lecithin containing different acyloxy groups, e.g. 1-palmitoyl-2-oleoyl lecithin, or a cephalin such as a natural cephalin, e.g. egg cephalin or a cephalin containing different acyloxy groups, e.g. 1-palmitoyl-2-oleoylcephalin, or a phosphatidiylserine, e.g. a natural phosphatidylserine such as beef brain phosphatidylserine, or a synthetic phosphatidylserine, e.g. dipalmitoylphosphatidylserine, a monoglyceride, e.g. monoolein or monomyristin, or a sterol, e.g. cholesterol.

To obtain unilamellar liposomes, a homogeneous layer of the lipid components is first prepared. The preparation of the homogeneous layer can be effected in a manner which is known per se and is described subsequently in the section entitled "Preparation of the homogeneous layer of the lipid components".

The homogeneous layer is dispersed in aqueous phase and the pH of such aqueous phases, in which only one lipid component, e.g. pure phosphatidic acid, is dispersed, is thereafter raised to about 12, preferably to about 9-11. This is accomplished e.g. by addition of physiologically acceptable basic solutions, e.g. dilute aqueous sodium hydroxide or potassium hydroxide solution (about 0.01 to 0.2N, preferably about 0.1N), while simultaneously controlling the pH value, e.g. by spot test or a pH meter. In aqueous phases in which several lipid components, e.g. phosphatidic acid and lecithin, are dispersed, an increase in the pH value to about 8-9 suffices. This pH range can also be adjusted by addition of an aqueous base, e.g. dilute sodium hydroxide or potassium hydroxide solution, while simultaneously controlling the pH, or by addition of a buffer solution, e.g. phosphate buffer solution with a suitable pH value of 7 to 8.

In a preferred embodiment of the invention, the homogeneous layer of the lipid components is dispersed in aqueous phases having a pH value higher than 7, e.g. in physiologically acceptable basic solutions, e.g. in dilute aqueous sodium hydroxide or potassium hydroxide solution (about 0.01 to 0.2N, preferably 0.1N). One lipid component, e.g. pure phosphatidic acid, will be dispersed in aqueous phases having a pH up to about 12, preferably about 9-11. Several lipid components, e.g. phosphatidic acid and lecithin, will be dispersed in aqueous phases having a pH of about 8 to 9.

Process (b)

For a lipid of the formula A, wherein m is 0 or 1, one of $R_1$ and $R_2$ is hydrogen, hydroxy or $C_1$-$C_4$alkyl, and the other is alkyl, alkenyl, alkoxy or alkenyloxy, each of 10 to 20 carbon atoms, $R_3$ is hydrogen and $R_4$ is lower alkyl substituted by an ammonio group, $R_1$ and $R_2$ have the particular and preferred meanings assigned to them under process (a).

$R_4$ as lower alkyl substituted by an ammonio group is e.g. lower alkyl substituted by a tri-lower alkylammonio group such as trimethylammonio or triethylammonio, and is e.g. 2-trimethylammonioethyl or 2-triethylammonioethyl.

For a lipid of the formula A, wherein m is 0 or 1, each of $R_1$ and $R_2$ independently of the other is alkyl, alkenyl, alkoxy, alkenyloxy each of 10 to 20 carbon atoms, or acyloxy of 10 to 50 carbon atoms, $R_3$ is hydrogen and $R_4$ is lower alkyl substituted by an ammonio lower alkylammonio group, $R_1$ and $R_2$ have the particular and preferred meanings assigned to them under process (a).

Lower alkyl substituted by an ammonio-lower alkylammonio group is e.g. 2-[N,N-di-lower alkyl-N-(2-N',N',N'-trilower alkylammonioethyl]ammonio)ethyl such as 2-[N,N-dimethyl-N-(2-N',N',N'-trimethylammonioethyl)ammonio]ethyl.

A suitable additional lipid is one of the additional lipids referred to hereinbefore under process (a).

The aqueous dispersion preferably contains a lipid of the formula A, wherein m is 1, $R_1$ is acyloxy, e.g. lauroyloxy, myristoyloxy, palmitoyloxy or stearoyloxy, $R_2$ is hydroxy, $R_3$ is hydrogen and $R_4$ is trimethylammonioethyl, and a suitable additional lipid of the formula A, wherein $R_1$ and $R_2$ are acyloxy, e.g. lauroyloxy, myristoyloxy, palmitoyloxy or stearoyloxy, $R_3$ is hydrogen and $R_4$ is 2-aminoethyl or 2-trimethylammonioethyl. The aqueous dispersion may also preferably contain a lipid of the formula A, wherein $R_1$ and $R_2$ are acyloxy, e.g. lauroyloxy, myristoyloxy, palmitoyloxy or stearoyloxy, $R_3$ is hydrogen and $R_2$ is 2-[N,N-dimethyl-N-(2-N',N',N'-trimethylammonioethyl)ammonio]ethyl, and optionally an additional lipid of the formula A, wherein $R_1$ and $R_2$ are acyloxy, e.g. lauroyloxy, myristoyloxy, palmitoyloxy or stearoyloxy, $R_3$ is hydrogen and $R_4$ is 2-aminoethyl or 2-trimethylammonioethyl.

In particular, the aqueous dispersion contains a lysophatidylcholine (lysolecithin) and a natural lecithin, e.g. egg lecithin. The aqueous dispersion may also preferably contain a phosphatidyl-2-[N,N-dimethyl-N-(2-N',-N',N'-trimethylammonioethyl)ammonio]ethyl chloride and optionally a natural lecithin, e.g. egg lecithin.

To obtain unilamellar liposomes, a homogeneous layer of the lipid components is first prepared, e.g. lysolecithin or phosphatidyl-2-[N,N-dimethyl-N-(2-N',N',N'-trimethylammonioethyl)ammonio]ethyl chloride. The preparation of the homogeneous layer can be effected in a manner known per se and is described below in the section entitled "Preparation of the homogeneous layer of lipid components".

The homogeneous layer is dispersed in aqueous phase and the pH is then lowered to about 1 or below while simultaneously controlling the pH value, e.g. by drop tests or with a pH meter. This is done e.g. by adding a physiologically acceptable acid, e.g. a dilute aqueous mineral acid such as dilute aqueous sulfuric, hydrochloric or phosphoric acid.

In a preferred embodiment of the invention, the homogenous layer of lipid components is dispersed in an aqueous phase having a pH of about 1 or below, e.g. in a dilute aqueous mineral acid such as dilute aqueous sulfuric, hydrochloric or phosphoric acid while simultaneously controlling the pH value.

Subsequent neutralisation of the aqueous phase is necessary if the pH of the aqueous phase has been adjusted beforehand in accordance with process (a) to a value higher than 8 or, in accordance with process (b), to a value lower than 5. This neutralisation is carried out in order to avoid decomposition of the drug and/or of the liposomes under basic or acid conditions directly after lowering or raising the pH value. The basic aqueous phase is neutralised with a physiologically acceptable acid or with a buffer solution, e.g. a phosphate buffer solution having a pH value of 7 to 8. Examples of suitable acids are the dilute aqueous mineral acids referred to above as well as weak organic acids, e.g. formic acid or acetic acid. The acidic aqueous phase is neutralised by addition of an aqueous base, e.g. dilute aqueous sodium hydroxide or potassium hydroxide solution. Neutralisation is effected while simultaneously controlling the pH value.

The lipids are dispersed in the aqueous phase in concentrations of up to more than 70%. The preferred concentration range is from about 1% to about 20%.

The process is conveniently carried out at room temperature or at elevated temperature, e.g. up to about 60° C. If the sensitivity of the drug to be encapsulated requires it, the process is carried out with cooling and optionally in an inert gas atmosphere, e.g. in a nitrogen atmosphere.

Both in process (a) and in process (b), the formation of unilamellar liposomes occurs spontaneously (spontaneous vesiculation), i.e. without the additional supply of external energy and at high rate. The unilamellar liposomes obtainable by processes (a) and (b) are stable for a relatively long period of time in aqueous phase. For example, unilamellar liposomes consisting of egg phosphatidic acid or egg phosphatidic acid and egg lecithin remain stable in aqueous phase at 4° C. for more than 14 days. Aqueous phases containing unilamellar liposomes obtainable by the process of this invention can be made storage stable by the process disclosed in European patent application No. 0 065 292. The formation of unilamellar liposomes and the content thereof in aqueous phase can be determined in a manner known per se by means of different methods, e.g. optically by electron microscopy, by mass analysis in the analytical ultracentrifuge, in particular, by spectroscopy, e.g. in the nuclear resonance spectrum $^1H$, $^{13}C$ and $^{31}P$). For example, sharp signals in the nuclear resonance spectrum indicate the formation of small unilamellar liposomes. The amount of small unilamellar liposomes in the system can be calculated from the intensity of the signals. Thus in the proton nuclear resonance spectrum, a sharp methylene signal at $\delta=1.28$ ppm and a sharp methyl signal at $\delta=0.89$ ppm is characteristic for small unilamellar liposomes which are formed from phosphatidic acid. The methylene and methyl signal at $\delta=1.28$ ppm and 0.89 ppm respectively, and additionally a methyl signal at $\delta=3.23$, which is assigned to the trimethylammonio group of lecithin, likewise indicate small unilamellar liposomes consisting of phosphatidic acid and lecithin.

The size of the unilamellar liposomes depends, inert alia, on the structure of the lipid components, on the ratio of the lipid components, on the concentration of these lipid components in the aqueous phase, and on the amount and structure of the drug to be encapsulated. Thus, for example, aqueous phases having a high concentration of small or large unilamellar liposomes can be prepared by varying the concentration of the lipid components. For example, the number of LUL in a disperse phase can also be increased by the addition of salts, e.g. NaCl or KCl. The diameter of the SUL formed e.g. from phosphatidic acid or phosphatidic acid and lecithin is about 200 to 600 Å. The encapsulation volume of SUL of this size is about 1 liter per mole of lipid component employed.

In addition to SUL, large unilamellar liposomes (LUL diameter up to about 50,000 Å) are also formed. These encapsulate larger volumes per mole of lipid components employed and are suitable for encapsulation with higher yield and for encapsulating voluminous substances, e.g. viruses, bacteria or cell organellae.

The separation of SUL from LUL is accomplished by conventional separation methods such as gel filtration, e.g. with Sepharose 4B as carrier, or by sedimentation of the LUL in an ultracentrifuge at 160,000×g. For example, the LUL deposit after centrifugation for several hours, e.g. about 3 hours, in this gravitional field, whereas the SUL remain in dispersion and can be decanted. Complete separation of the LUL from the SUL is achieved after repeated centrifugation.

All liposomes having a diameter greater than 600 Å present in the aqueous phase, e.g. LUL or multilamellar liposomes, as well as non-encapsulated drugs and excess dispersed lipids, can also be separated by gel filtration, so making it possible to obtain an aqueous phase containing a fraction of SUL of relatively uniform size.

The liposomes obtainable by the process of this invention (SUL and LUL) are suitable carrier systems which, in aqueous phase, may be used for solubilising lipophilic substances, e.g. fat-soluble dyes, for stabilising substances which are sensitive to hydrolysis, e.g. prostaglandins, for encapsulating pesticides, e.g. for modifying the activity spectrum of dichlorphos, for encapsulating food additives, e.g. to modify the adsorption properties of vitamins or dyes, or for introducing encapsulated drugs, enzymes, antibodies, hormones, genes, viruses, vitamins or cell organellae into the cells of a cell culture.

Aqueous phases which contain the liposomes obtainable by the process of the invention with encapsulated drugs are delivery systems which are suitable, optionally after concentration or isolation of the liposomes, e.g. by ultracentrifugation, for therapeutic purposes for oral (p.o.), parenteral (i.v. or i.p.) or topical administration.

In oral administration, liposome-based delivery systems can protect an active ingredient, e.g. insulin, which is unstable in the digestive tract, or improve its resorption. For oral administration, the liposome-containing aqueous phase can be mixed with pharmaceutically acceptable diluents or carriers or with conventional additives such as dyes or flavourings, and administered as syrup or in the form of capsules.

For parenteral administration, liposome-based delivery systems can prolong the retention time e.g. of desferrioxamin (q.v. R. A. Guilmette et al., Lif Sci. 22 (4), 313–320, 1978) or gentamycin (q.v. W. M. Scheld et al., Clin. Res. 26, No. 1, 59 A, 1978), in an organism. The retention time of entrapped chelating agents, e.g. EDTA (ethylenediaminetetraacetic acid), in organisms is prolonged in the same manner, so that heavy metals can be removed by chelation especially from the liver, spleen or kidneys (q.v. Rahmann et al., Science, Vol. 180, 300–302, 1973, and J. Lab. Clin. Med. 640–647, 1974). With liposome-based delivery systems it is possible to enrich drugs in the myocardium (q.v. Landesmann et al., Science, Vol. 198, 737–738, 1977). It is possible to enrich antiflammatory drugs, e.g. cortisol (q.v. Nature 271, No. 5643, 372–73, 1978) or protease inhibitors (q.v. Anal. Biochem. 89, No. 2, 400–07, 1978) in the synovial fluid, and cytostatic drugs in tumour tissue (q.v. the article entitled "Liposomes—Problems and promise as selective drug carriers" by Stanley B. Kaye in Cancer Treatment Reviews 8, 27–50, 1981, and the many references cited therein). Many chemotherapeutic drugs employed in cancer therapy are less toxic and better tolerated if they are encapsulated in liposomes, e.g. liposome-encapsulated Actinomycin D (q.v. Rahmann et al., Proceedings of the Society for Experimental Biology and Medicine 146, 1173–1176, 1974), Methotrexate (q.v. L. D. Lasermann et al., Proc. Natl. Acad. Sci. 77, No. 7, 4089–93, 1980), Vinblastin, Daunomycin or cytosin-arabinoside (q.v. Mühlensiepen et al., Cancer Res. 41, No. 5, 1602–07, 981). Liposomes can be used for introducing e.g. enzymes, peptide hormones, genes or viruses into the cytoplasma of cells in living organisms, e.g. for introducing aspariginase (q.v. the article entitled "The Introduction of enzymes into cells by means of liposomes" by M. Finkelstein and G. Weissmann in J. Lipid Research, Vol. 19, 1978, 289–303), of amyloglucosidase (q.v. G. Gregoriadis and B. E. Ryman, Eur. J. Biochem 24 (1972), 485–491, or neuromidase (q.v. Gregoriadis et al., Biochem. J. (1974) 140, 232–330), for bonding specific detection molecules, e.g. monoclonal antibodies, for specific introduction into defined target cells (q.v. Lesermann et al., Nature 292 (5829), 226–228, 1981), for immunostimulation as adjuvant for inoculations, e.g. against leishmaniasis (q.v. New, R. R. C. et al., Nature 272 (5648) 55–56, 1978), or for the induced release of drugs by signals such as temperature increases, e.g. in inflamed tissue, or changes in pH values. For parenteral administration, the concentrated or isolated liposomes can be suspended in a suitable carrier liquid, for example in sterile distilled water or in physiological sodium chloride solution.

Preparation of the Homogeneous Layer of Lipid Components

The homogeneous layer of lipid components can be prepared in a manner which is known per se. For example, the lipid or mixture of lipids of the formula A, e.g. pure egg phosphatidic acid or a mixture of egg phosphatidic acid and egg lecithin, optionally in admixture with a lipophilic active ingredient, e.g. a protein which is encapsulated during the formation of the liposome in the lipid layer, is dissolved in an organic solvent. A homogeneous layer of lipid components is obtained by removing the organic solvent, most conveniently in vacuo or by blowing off with an inert gas, e.g. nitrogen.

The choice of solvent depends on the solubility of the particular lipid components therein. Examples of suitable solvents are: halogenated, aliphatic, cycloaliphatic, aromatic or aromatic-aliphatic hydrocarbons, e.g. benzene, toluene, methylene chloride or chloroform; alcohols, e.g. methanol or ethanol; lower alkanecarboxylates, e.g. ethyl acetate; ethers, e.g. diethyl ether, dioxan or tetrahydrofuran; or mixtures of these solvents.

The lipids referred to in the description of this invention are known or, if novel, can be prepared in a manner known per se in accordance with the particulars set forth in the standard work by C. G. Knight, Liposomes, Chapter 3, Elvesier Press, 1981. All the lipids mentioned can be present in the aqueous dispersion in the form of optically active derivatives or as racemates. The following Examples illustrate the invention, without implying any restriction to what is disclosed therein. Ratios are volume ratios.

EXAMPLE 1

(a) 1 g of egg phosphatidic acid is dissolved in 20 ml of a 2:1 mixture of chloroform/methanol and the solution is concentrated in vacuo in a rotary evaporator. The film-like residue is dispersed in 20 ml of distilled water by shaking for 5 minutes. The resultant dispersion has a pH of about 3. Unilamellar liposomes are obtained by then adding to the dispersed phase, at room temperature and while controlling with a pH meter, 0.1N sodium hydroxide solution until the pH rises to 11. The pH of the aqueous phase is subsequently lowered from 11 to about 7 by adding 0.1N HCl. A slightly opalescent aqueous phase is obtained.

The unilamellar liposomes so obtained can be made visible in an electron microscope. The liposome dispersion is first subjected to conventional freeze-fracture. There are obtained mainly two "populations" of liposomes, which differ by their average size:

1. small unilamellar liposomes (SUL) having a diameter of about 200 to 600 Å and
2. large unilamellar liposomes (LUL) having a diameter of about 1000 to 10,000 Å.

SUL are detectable in the proton NMR spectrum by the signals $\delta=1.28$ (methylene) and $\delta=0.89$ (methyl). The yield of SUL can be assessed from the intensity of the signals and is about 56%.

(b) In the same manner as described in (a), $4\times10$ mg of egg phosphatidic acid are dissolved in $4\times0.2$ ml of a 2:1 mixture of chloroform/methanol and the solutions are concentrated in vacuo. Each of the film-like residues is dispersed in 1 ml of distilled water by shaking for 5 minutes. Unilamellar liposomes are obtained by then adding to each individual disperse phase, while controlling with a pH meter, 0.1N sodium hydroxide solution until a final pH of 6, 8, 11.3 and 11.6 respectively is obtained. With increasing pH value, the respective yield of SUL for each sample is 5, 24, 57 and 60%.

EXAMPLE 2

(a) 1 g of egg phosphatidic acid is dissolved in 20 ml of a 2:1 mixture of chloroform/methanol and this solution is concentrated in vacuo. The film-like residue is dispersed by shaking it in 50 ml of a 0.01N sodium hydroxide solution and the dispersion so obtained has a pH of about 12. The pH of the aqueous dispersion is then lowered to about 7-8 by addition of 0.1N hydrochloric acid. The yield of SUL is about 100%.

(b) Following the procedure described in Example 2(a), $4\times10$ mg of egg phosphatidic acid are dissolved in $4\times0.2$ ml of a 2:1 mixture of chloroform/methanol and these solutions are concentrated in vacuo. Each sample is dispersed by shaking it in sufficient 0.01N sodium hydroxide solution and distilled water to give pH values of about 7.3, 8.0, 9.4 and 10.0 respectively. With increasing pH value, the yield of SUL for each sample is 33, 46, 65 and 81%.

EXAMPLE 3

0.1 g of dilauroylphosphatidic acid is dissolved in 5 ml of a 2:1 mixture of chloroform/methanol and the solution is concentrated iu vacuo. The film-like residue is dispersed in 50 ml of a 0.01N sodium hydroxide solution by shaking and the resultant dispersion has a pH of about 12. The pH of the aqueous dispersion is then lowered to about 7-8 by addition of 0.1N hydrochloric acid. The yield of SUL (diameter about 300–800 Å) is 73%.

EXAMPLE 4

(a) 3 mg of egg phosphatidic acid and 7 mg of egg lecithin are dissolved in 0.5 ml of a 2:1 mixture of chloroform/methanol and this solution is concentrated in vacuo. The film-like residue is dispersed in 1 ml of distilled water by shaking for 5 minutes at room temperature. The pH of the resultant dispersion is about 3. Unilamellar liposomes are obtained by then adding, at room temperature and while controlling with a pH meter, 0.1 1N sodium hydroxide solution until the pH rises to about 11.2. The pH of the aqueous phase is then adjusted to about 7 with phosphate buffer solution. A slightly opalescent aqueous phase is obtained. The formation of unilamellar liposomes can be detected in the NMR spectrum by the signal $\delta=1.28$ (methylene), $\delta=0.89$ (methyl) and $\delta=3.23$ (N—CH$_3$). The electron micrograph shows principally two "populations" of unilamellar liposomes which differ in their average size:

1. SUL having a diameter of about 200–800 Å and
2. LUL having a diameter of about 1000–10,000 Å.

The yield of SUL is 45%.

(b) Following the procedure described in Example 4(a), $2\times3$ mg of egg phosphatidic acid and 7 mg of egg lecithin are dissolved in $2\times0.5$ ml of a 2:1 mixture of chloroform/methanol. Each of the film-like residues is dispersed in 1.0 ml of distilled water by shaking for 5 minutes. Unilamellar liposomes are obtained by then adding to each individual phase, while controlling with a pH meter, sufficient 0.1N sodium hydroxide solution, with shaking, to give final pH values of 8.6 and 10 respectively. With increasing pH value, the respective yield of SUL is 22 and 35%.

(c) Following the procedure described in (a), samples of different concentration of egg phosphatidic acid and egg lecithin are each dissolved in 0.5 ml of a 2:1 mixture of chloroform/methanol and these solutions are concentrated in vacuo. Each of the film-like residues is dispersed in 1.0 ml of distilled water by shaking for 5 minutes. Unilamellar liposomes are obtained by then adding to each individual phase, while controlling with a pH meter, sufficient 0.1N sodium hydroxide solution, with shaking, to give a final pH value of about 11.2. With increasing concentration of egg phosphatidic acid, the yield of SUL for each sample is:

| egg phosphatidic acid (%) | 6 | 10 | 14 | 20 | 25 | 30 | 33 | 50 | 48 | 60 |
|---|---|---|---|---|---|---|---|---|---|---|
| SUL (%) | 5 | 9 | 14 | 17 | 19 | 20 | 27 | 39 | 41 | 50 |

EXAMPLE 5

(a) 0.3 g of egg phosphatidic acid and 0.7 g of egg lecithin are dissolved in 10 ml of a 2:1 mixture of chloroform/methanol and the solution is concentrated in vacuo. The residue is dispersed in 10 ml of 0.01N sodium hydroxide solution by shaking. The resultant dispersion has a pH of about 12. The pH of the aqueous dispersion is then lowered to about 7-8 by addition of 0.1N hydrochloric acid. The yield of SUL is about 30%.

(b) Following the procedure of (a), samples of different content of egg phosphatidic acid and egg lecithin (total of 10 mg of lipid) are each dissolved in 0.5 ml of a 2:1 mixture of chloroform/methanol and the solution is concentrated in vacuo. Each of the film-like residues is dispersed in 1 ml of 0.01N sodium hydroxide solution by shaking. The dispersions have a pH of about 12. The pH of each aqueous dispersion is lowered to about 7–8. With increasing concentration of egg phosphatidic acid, the yield of SUL for each sample is:

| egg phosphatidic acid (%) | 10 | 20 | 25 | 30 | 40 | 50 | 60 | 80 |
|---|---|---|---|---|---|---|---|---|
| SUL (%) | 14 | 22 | 31 | 42 | 45 | 50 | 78 | 95 |

EXAMPLE 6

0.7 g of egg lecithin, 0.3 g of beef brain phosphatidylserine and 2 g of egg phosphatidic acid are dissolved in 20 ml of a 2:1 mixture of chloroform/methanol, and the solution is concentrated in vacuo in a rotary evaporator. The film-like residue is dispersed in 100 ml of 0.01N sodium hydroxide solution by shaking for 5 minutes at room temperature. The dispersion has a pH of about 12. The pH of the aqueous phase is then adjusted to about 7 by addition of 1N hydrochloric acid. A slightly opalescent aqueous phase is obtained.

The formation of unilamellar liposomes can be detected spectroscopically as in Example 1a), e.g. by NMR or electron microscopy. LUL and SUL are visible in the electron micrograph.

(b) Following the procedure of (a), samples having a different concentration of egg phosphatidic acid, but having the same concentration of egg lecithin and phosphatidylserine (total of 10 mg of lipid), are each dissolved in 0.5 ml of a 2:1 mixture of chloroform/methanol and these solutions are concentrated in vacuo. Each of the residues is dispersed in 1.0 ml of 0.1N sodium hydroxide solution by shaking, and the resultant dispersion has a pH of about 12. The pH of the aqueous dispersion is then lowered to about 7–8 by addition of 0.1N hydrochloric acid. With increasing concentration of egg phosphatidic acid, the yield of SUL for each sample is:

| egg phosphatidic acid (%) | 9 | 10 | 26 | 33 | 34 | 40 | 60 |
|---|---|---|---|---|---|---|---|
| SUL (%) | 14 | 18 | 26 | 36 | 47 | 43 | 64 |

EXAMPLE 7

1 g of asolectin (mixture of phospholipids consisting mainly of lecithin, cephalin, phosphatidylserine and phosphatidylinositol) and 0.2 g of egg phosphatidic acid are dissolved in 20 ml of a 2:1 mixture of chloroform/methanol and the solution is concentrated in vacuo. The film-like residue is dispersed in 100 ml of 0.01N sodium hydroxide solution by shaking for 5 minutes at room temperature. The resultant dispersion has a pH of about 12. The pH of the aqueous phase is then lowered to about 7 by addition of 1N hydrochloric acid. A slightly opalescent aqueous phase is obtained.

The formation of unilamellar liposomes can be detected as in Example 1(a) spectroscopically, e.g. by NMR or electron microscopy. SUL and LUL are visible in the electron micrograph.

(b) Following the procedure of Example 6(a), samples having a different concentration of egg phosphatidic acid, but containing an identical amount of asolectin (total of 10 mg of lipid), are each dissolved in 0.5 ml of a 2:1 mixture of chloroform/methanol and the solutions are concentrated in vacuo. Each residue is dispersed in 1 ml of 0.01N sodium hydroxide solution by shaking and the resultant dispersion has a pH of about 12. The pH of the aqueous dispersion is then lowered to about 7–8 by addition of 0.1N hydrochloric acid. With increasing concentration of egg phosphatidic acid, the yield of SUL for each sample is:

| egg phosphatidic acid (%) | 17 | 37 | 50 |
|---|---|---|---|
| SUL (%) | 24 | 69 | 65 |

EXAMPLE 8

(a) 0.1 g of a mixture of egg lecithin and cholesterol (molar ratio 1:1) and 0.1 g of egg phosphatidic acid are dissolved in 10 ml of a 2:1 mixture of chloroform/methanol and the solution is concentrated in vacuo. The film-like residue is disPersed in 10 ml of 0.01N sodium hydroxide solution by shaking for 5 minutes at room temperature. The resultant dispersion has a pH of about 12. The pH of the aqueous phase is then lowered to about 7 by addition of 1N hydrochloric acid. A slightly opalescent aqueous phase is obtained.

The formation of unilamellar liposomes can be detected as in Example 1(a) by spectroscopy, e.g. by NMR or electron microscopy.

(b) Following the procedure of Example 8(a), samples having a different concentration of egg phosphatidic acid, but containing the same amount of egg lecithin and cholesterol (total of 10 mg of lipid), are each dissolved in 0.5 ml of a 2:1 mixture of chloroform/methanol and the solutions are concentrated in vacuo. Each residue is then dispersed in 1,0 ml of 0.01N sodium hydroxide solution by shaking, whereupon the pH of the dispersion rises to about 12. The pH of the aqueous dispersion is then lowered to about 7–8 by addition of 0.1N hydrochloric acid. With increasing concentration of egg phosphatidic acid, the yield of SUL for each sample is:

| egg phosphatidic acid (%) | 10 | 30 | 50 | 80 |
|---|---|---|---|---|
| SUL (%) | 4 | 10 | 20 | 50 |

EXAMPLE 9

0.5 g of egg phosphatidic acid and 0.5 g of dimyristoyl lecithin are dissolved in 10 ml of 2:1 of chloroform/methanol and the solution is concentrated in vacuo. The film-like residue is dispersed in 50 ml of 0.01N sodium hydroxide solution, and the pH of the dispersion is about 12. The pH of the aqueous dispersion is then lowered to about 7–8 by addition of 0.1N hydrochloric acid. The yield of SUL is 36%.

EXAMPLE 10

Following the procedure of Example 9, mixtures of liposomes consisting of 0.5 g of egg phosphatidic acid and 0.5 g of dipalmitoyl lecithin or of distearyl lecithin are prepared. The yield of SUL is 10%.

EXAMPLE 11

Following the procedure of Example 9, a mixture of liposomes consisting of 0.5 g of dipalmitoyl phosphatidic acid and 0.5 of egg lecithin is prepared. The yield of SUL is 10%.

EXAMPLE 12

5 mg of lysolecithin and 5 mg of egg lecithin are dissolved in 1 ml of a 2:1 mixture of chloroform/methanol and the solution is concentrated in vacuo. The film-like residue is dispersed in 1 ml of distilled water by shaking for 5 minutes. The dispersion has a pH of about 5–7. Unilamellar liposomes are formed by then adding to the aqueous dispersion at room temperature and while controlling with a pH meter, sufficient 0.1N hydrochloric acid to lower the pH of the aqueous phase to 0.5. The pH is subsequently raised to 7 by addition of 0.1N sodium hydroxide solution.

The formation of unilamellar liposomes can be detected as in Example 1a) spectroscopically, e.g. by NMR or electron microscopy. SUL and LUL are observed in the electron micrograph. The yield of SUL is 50%.

EXAMPLE 13

Following the procedure of Example 12, a mixture of liposomes consisting of phosphatidyl 2-[N,N-dimethyl-N-(2-N',N',N'-trimethylammonioethyl)ammonio]ethyl chloride (the preparation of which is described by C. G. Knight, Liposomes, Chapter 3, Elsevier 1981) and 5 mg of egg lecithin is prepared.

The formation of unilamellar liposomes can be detected spectroscopically as in Example 1(a), e.g. by NMR or electron microscopy. SUL having a diameter of 250 Å and LUL having a diameter of about 600 to 10,000 Å can be observed in the electron micrograph. The yield of SUL is 50%.

EXAMPLE 14

5 mg (6.67 mmoles) of egg lecithin and 5 mg (9.5 mmoles) of natural lysophosphatidyl glycerol are dissolved in 1 ml of a 2:1 mixture of chloroform/methanol and the solution is concentrated in vacuo in a rotary evaporator. The film-like residue is dispersed in 1 ml of distilled water. The dispersion has a pH of about 5. The pH of the aqueous dispersion is then adjusted to about 8 with 0.1N sodium hydroxide solution while controlling with a pH meter.

The formation of unilamellar liposomes can be detected spectroscopically as in Example 1(a), e.g. by NMR or electron microscopy. SUL and LUL are observed in the electron micrograph. The yield of SUL is about 35%.

EXAMPLE 15

6 mg (8.0 mmoles) of egg lecithin and 4 mg (8.0 mmoles) of natural lysophosphatidylserine are dissolved in 1 ml of a 2:1 mixture of chloroform/methanol and the solution is concentrated in vacuo in a rotary evaporator. The film-like residue is dispersed in 1 ml of distilled water by shaking for 5 minutes. The dispersion has a pH of about 6. The pH of the aqueous dispersion is then adjusted to about 8 with 0.1N sodium hydroxide solution while controlling with a pH meter.

The formation of unilamellar liposomes can be detected spectroscopically as in Example 1(a), e.g. by NMR or electron microscopy. SUL and LUL are observed in the electron micrograph. The yield of SUL is about 20%.

EXAMPLE 16

5 mg (6.67 mmoles) of egg lecithin and 5 mg (10.0 mmoles) of lysophosphatidyl inositol are dissolved in 1 ml of a 2:1 mixture of chloroform/methanol and the solution is concentrated in vacuo in a rotary evaporator. The film-like residue is dispersed in 1 ml of distilled water by shaking for 5 minutes. The dispersion has a pH of about 6. The pH of the aqueous dispersion is then adjusted to about 7 with 0.1N sodium hydroxide solution while controlling with a pH meter.

The formation of unilamellar liposomes can be detected spectroscopically as in Example 1(a), e.g. by NMR or electron microscopy. SUL and LUL are observed in the electron micrograph. The yield of SUL is about 40%.

EXAMPLE 17

(a) 0.5 g of monoolein (9-cis-octadecenoyl glycerol) and 0.5 g of egg phosphatidic acid are dissolved in 20 ml of a 2:1 mixture of chloroform/methanol and the solution is concentrated in vacuo. The film-like residue is dispersed in 100 ml of 0.01N sodium hydroxide solution by shaking for 5 minutes at room temperature. The resultant dispersion has a pH of about 12. The pH of the aqueous phase is then lowered to about 7 by addition of 1N hydrochloric acid. A slightly opalescent aqueous phase is obtained.

The formation of unilamellar liposomes can be detected as in Example 1(a) by spectroscopy, e.g. by NMR or electron microscopy. LUL and SUL are observed in the electron micrograph.

(b) Following the procedure of Example 17(a), samples having a different concentration of egg phosphatidic acid and monoolein (total of 10 mg of lipid) are each dissolved in 0.5 ml of a 2:1 mixture of chloroform/methanol and the solutions are concentrated in vacuo. Each residue is dispersed in 1 ml of 0.01N sodium hydroxide solution by shaking and the resultant dispersion has a pH of about 12. The pH of the aqueous dispersion is then lowered to about 7–8 by addition of 0.1N hydrochloric acid. With increasing concentration of egg phosphatidic acid, the yield of SUL for each sample is:

| egg phosphatidic acid (%) | 20 | 30 | 50 | 80 |
|---|---|---|---|---|
| SUL (%) | 10 | 17 | 26 | 45 |

EXAMPLE 18

Following the procedure of Example 17(a), samples having a different concentration of egg phosphatidic acid and monomyristin (total of 10 mg of lipid), are each dissolved in 0.5 ml of a 2:1 mixture of chloroform/methanol and the solutions are concentrated in vacuo. Each residue is then dispersed in 1.0 ml of 0.01N sodium hydroxide solution by shaking and the resultant dispersion has a pH of about 12. The pH of the aqueous dispersion is then lowered to about 7–8 by addition of 0.1N hydrochloric acid. With increasing content of egg phosphatidic acid, the yield of SUL for each sample is;

| egg phosphatidic acid (%) | 30 | 50 | 80 |
|---|---|---|---|
| SUL (%) | 9 | 18 | 38 |

EXAMPLE 19

(a) Following the procedure of Example 1(a) and 1(b), a mixture of liposomes consisting of egg phosphatidic acid is prepared to give a yield of 66% of SUL. To increase the content of LUL in the mixture of liposomes, 0.5 molar sodium chloride solution is added to the disperse phase which contains freshly prepared unilamellar liposomes. The content of SUL falls with increasing concentration of NaCl in the disperse phase:

| [NaCl] in mole/l | 0 | 0.2 | 0.3 | 0.4 | 0.5 | 0.6 | 0.75 | 0.95 |
|---|---|---|---|---|---|---|---|---|
| SUL (%) | 66 | 64 | 50 | 40 | 30 | 23 | 15 | 11 |

(b) To increase the content of LUL in the mixture of liposomes, 0.5 molar potassium chloride solution is added to the disperse phase which contains freshly prepared unilamellar liposomes consisting of pure egg phosphatidic acid. The concentration of SUL decreases with increasing concentration of KCl in disperse phase.

| [KCl] in mole/l | 0 | 0.2 | 0.4 | 0.5 | 0.63 |
|---|---|---|---|---|---|
| SUL (%) | 66 | 63 | 50 | 50 | 36 |

EXAMPLE 20

40 mg of dipalmitoylphosphatidylcholine and 20 mg of egg phosphatidic acid are dissolved in 5 ml of pure tert-butanol at 60° C. The solution is frozen by immersing the flask in a freezing mixture of methanol/dry ice. The tert-butanol is removed in a freeze drier to obtain a homogeneous foam of lipids. This foam is then dispersed in water by vigorous shaking. Unilamellar liposomes are formed by adding, at room temperature and while controlling with a pH meter, sufficient 0.1N sodium hydroxide solution to raise the pH to about 8. The pH of the aqueous phase is then adjusted to about 7 by addition of a phosphate buffer solution. A slightly opalescent aqueous phase is obtained. The liposomes so obtained can be observed under the electron microscope and have a diameter of 200 to 10,000 Å.

EXAMPLE 21

3.0 mg of one of the lipids listed in the following table and 7.0 mg of egg lecithin are dissolved in 1 ml of a 2:1 mixture of chloroform/methanol and the solution is concentrated. The film-like residue is dispersed in 1 ml of distilled water. The pH of the dispersion is in the range from about 6 to 10. Then the pH of the aqueous phase is increased to about 8 by addition of 0.1N sodium hydroxide solution. The formation of unilamellar liposomes can be detected spectroscopically as in Example 1(a), e.g. by NMR or electron microscopy. LUL and SUL are observed in the electron micrograph. The yield of SUL is indicated in the table:

| Lipid | concentration of the lipid [mM/l] | yield [% SUL] |
|---|---|---|
| 2-hydroxyethyl-3-palmitoyloxyphosphate | 6.52 | 40 |
| 2-methyl-2-palmitoyloxypropylhydrogenphosphate | 6.76 | 60 |
| 3-cetyloxypropyl-2-hydroxyethylphosphate | 6.73 | 35 |
| 2-bromoethylcetylphosphate | 6.63 | 55 |
| n-eicosyl-2,3-(2,2-propylene)-dioxypropylphosphate | 5.84 | 40 |
| 3-stearyloxypropylhydrogenphosphate | 5.98 | 55 |
| 2,3-dihydroxypropylmyristylphosphate | 7.69 | 40 |
| 3-cetyloxypropylhydrogenphosphate | 7.46 | 20 |
| 2,3-dihydroxypropyl-n-eicosylphosphate | 6.33 | 7 |
| cholesteryl-2,3-dihydroxypropylphosphate | 5.18 | 70 |
| cetyl-2,3-dihydroxypropylphosphate | 7.18 | 20 |
| ethyl-3-stearoyloxypropylphosphate | 6.36 | 40 |

EXAMPLE 22

Following the procedure of Examples 1 to 20, unilamellar liposomes can be prepared from nyristic acid and egg lecithin, myristic acid and egg cephalin, dimyristoylphosphatidic acid and dimyristoyl lecithin, dipalmitoylphosphatidic acid and 1-palmitoyl-2-oleoyl lecithin, 1-palmitoyl-2-oleoylphosphatidic acid and dipalmitoyl lecithin, 1-palmitoyl-2-oleoylphosphatidic acid and 1-palmitoyl-2-oleoyl lecithin, egg lysophosphatidic acid and egg lecithin, 1-myristoyl-lysophosphatidic acid and 1-palmitoyl-2-oleoyl lecithin, 1-palmitoyl-lysophosphatidic acid and 1-palmitoyl-2-oleoyl lecithin, beef brain lysophosphatidylserin and egg lecithin, 1-palmitoyl-lysophosphatidylserine, 1-palmitoyl-2-oleoyl-phosphatidylserine and 1-palmitoyl-2-oleoyl lecithin and beef brain lysophosphatidylserine and egg cephalin.

EXAMPLE 23

2 mg of hydrocortisone-21-palmitate, 40 g of egg lecithin and 20 mg of egg phosphatidic acid are dissolved in 5 ml of tert-butanol. The solution is filtered under sterile conditions through a 0.2 $\mu$m filter, filled into a 25 ml vial, frozen by immersing the vial in a freezing mixture of dry ice/ethanol, and lyophilised. The resultant foam is dispersed in 5 ml of sterile distilled water by shaking for 10 minutes. The pH is adjusted to 10.5 by addition of 0.1N sodium hydroxide solution which has been filtered under sterile conditions and the dispersion is allowed to stand for 1 minute. Then 0.5 ml of a 10-fold concentrate of a phosphate-buffered isotonic solution of sodium chloride of pH 7.4 (PBS for injection purposes) is added. The dispersion so obtained is suitable for injection into joint capsules in which inflammatory changes have occurred.

EXAMPLE 24

0.1 mg of N-acetylmuramyl-L-alanyl-D-isoglutamyl-L-alanyl-2-(1', 2'-dipalmitoyl-sn-glycero-3'-phosphoryl-)ethylamide, 7 mg of chromatographically pure egg albumin lecithin and 3 mg of egg phosphatidic acid are dissolved in 2 ml of a 2:1 mixture of chloroform/methanol. The solution is concentrated in vacuo and a clear lipid film remains as residue. This film is dispersed in 2 ml of sterile distilled water by shaking and one drop of 0.1% thymolphthalein solution is added. Then 0.1N sodium hydroxide solution is added until there is a change in colour, whereupon spontaneous vesiculation takes place. The pH is then buffered immediately to 7.4 by the addition of 0.2 ml of a 10-fold concentrate of phosphate-buffered isotonic solution of sodium chloride (PBS for injection purposes). The resultant dispersion is suitable for direct use for activating alveolar macrophages in cell cultures or in vivo in rats.

EXAMPLE 25

0.15 g of N-acetylmuramyl-L-alanyl-D-isoglutamyl-L-alanyl-2-(1′, 2′-dipalmitoyl-sn-glycero-3′-phosphoryl-)ethylamide, 27 g of egg lecithin containing 97% of phosphatidylcholine, and 3 g of egg phosphatidic acid are dissolved in a mixture of 200 ml of chloroform and 20 ml of methanol; 200 ml of tert-butanol are added and the solution is concentrated to 180 ml. The solution is filtered through a 0.2 μm filter under sterile conditions, rapidly frozen in a mixture of ethanol/dry ice, and subsequently lyophilised. The comminuted lyophilisate is added, with vigorous stirring, to 300 ml of sterile 0.01N sodium hydroxide solution and completely dispersed. The aqueous phase is neutralised with 0.1N HCl and the opalescent dispersion is filled into a stirred ultrafiltration cell (Amicon ®) which, instead of the ultrafilter, is provided with an even pore filter of polycarbonate (Nucleopore ®) which has a pore diameter of 0.1 μm, and has been washed free of particles. The dispersion is filtered under slight overpressure and with constant addition of Dulbecco's sterile buffer solution (pH 7.4 without Ca and Mg) so that the volume in the cell does not decrease to less than 300 ml. After the passage of 3 liters of filtrate, all the SUL are separated and the supernatant dispersion of LUL can be filled into ampoules and used for treatment assays.

EXAMPLE 26

15 mg of N-acetylmuramyl-L-alanyl-D-isoglutamyl-L-alanyl-2-(1′, 2′-dipalmitoyl-sn-glycero-3′-phosphoryl-)ethylamide, 0.6 g of pure egg lecithin and 2.4 g of egg phosphatidic acid are dissolved in a mixture of 20 ml of chloroform and 2 ml of methanol. The solution is filtered under sterile conditions through a 0.2 μm filter and concentrated with a rotary evaporator which has been deaerated over a sterile filter and washed free of particles in a 500 ml round flask such that the mixture of lipids dries on the walls of the flask in the form of a preferably uniform film. After the residue has been dried overnight in a high vacuum, 30 ml of sterile 0.01N sodium hydroxide are added and the flask is sealed and shaken for 5 minutes. The opalescent aqueous phase so obtained is adjusted to pH 7.4 by the addition of sterile 0.1N hydrochloric acid. The dispersion is filled into a stirred filter cell (total volume: 100 ml) as described in Example 23 and then filtered, while adding sterile water which has been filtered until free of particles, until 500 ml of filtrate have collected. This filtrate is fed continuously into a stirred filter cell equipped with an ultrafilter, e.g. Amicon U 10 ®, and then concentrated to a volume of 30 ml. The concentrated dispersion contains small unilamellar liposomes and, after addition of Dulbecco's phosphate buffer (pH 7.4, without Ca and Mg), is filled into ampoules and used for treatment assays.

What is claimed is:

1. A process for the spontaneous preparation of small unilamellar liposomes comprising, without additional energy input, dispersing
   (a) a homogeneous layer of a phospholipid of the formula

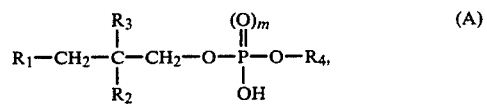

wherein m is zero or one, one of $R_1$ and $R_2$ is hydrogen, hydroxy or $C_1$-$C_4$-alkyl and the other is alkyl, alkenyl, alkoxy or alkenyloxy, each of 10-20 carbon atoms, or is acyloxy of 10-50 carbon atoms, $R_3$ is hydrogen or $C_1$-$C_4$-alkyl, and $R_4$ is hydrogen, $C_1$-$C_7$-alkyl, carboxy-lower alkyl, 2-aminoethyl, 3-amino-n-propyl, 2-methylaminoethyl, 3-methylamino-n-propyl, 2-dimethylaminoethyl, 3-dimethylamino-n-propyl, 2-amino-2-carboxyethyl, 3-amino-3-carboxy-n-propyl, 2-trimethylammonioethyl, 2-triethylammonioethyl, 3-tri-methylammonio-n-propyl, 3-triethylammonio-n-propyl, 2-hydroxyethyl, 2,3-dihydroxypropyl, 2-methoxyethyl, 3-methoxy-n-propyl, 2,3-ethylenedioxypropyl, 2,3-(2,2-propylene)dioxypropyl, 2-chloro- or 2-bromoethyl, 2- or 3-chloro-n-propyl or 2- or 3-bromo-n-propyl, or a carbohydrate radical of 5 to 12 carbon atoms, or, if $R_1$ and $R_2$ are hydrogen or hydroxy and $R_3$ is hydrogen, is a steroid radical, and an additional phospholipid of the formula A, wherein each of $R_1$ and $R_2$ independently of the other are alkyl, alkenyl, alkoxy or alkenyloxy, each of 10-20 carbon atoms, or is acyloxy of 10-50 carbon atoms, $R_3$ is hydrogen or $C_1$-$C_4$-alkyl and $R_4$ is $C_1$-$C_7$-alkyl, carboxy-lower alkyl, 2-aminoethyl, 3-amino-n-propyl, 2-methylaminoethyl, 3-methylamino-n-propyl, 2-dimethylaminoethyl, 3-dimethylamino-n-propyl, 2-amino-2-carboxyethyl, 3-amino-3-carboxy-n-propyl, 2-trimethylammonioethyl, 2-triethylammonioethyl, 3-trimethylammonio-n-propyl, 3-triethylammonio-n-propyl, 2-hydroxyethyl, 2,3-dihydroxypropyl, 2-methoxyethyl, 3-methoxy-n-propyl, 2,3-ethylenedioxypropyl, 2,3-(2,2-propylene)dioxypropyl, 2-chloro- or 2-bromoethyl, 2- or 3-chloro-n-propyl or 2- or 3-bromo-n-propyl, or a carbohydrate radical of 5 to 12 carbon atoms; or of a phospholipid of the formula A, wherein m is zero or one, each of $R_1$ and $R_2$ independently of the other is alkyl, alkenyl, alkoxy, or alkenyloxy, each of 10-20 carbon atoms, or is acyloxy of 10 to 50 carbon atoms, and $R_3$ and $R_4$ are hydrogen and optionally an additional phospholipid of the formula A wherein m is zero or one, each of $R_1$ and $R_2$ independently of the other is alkyl, alkenyl, alkoxy, or alkenyloxy, each of 10-20 carbon atoms, or is acyloxy of 10 to 50 carbon atoms, and $R_3$ is hydrogen or $C_1$-$C_4$-alkyl, and $R_4$ is $C_1$-$C_7$-alkyl, carboxy-lower alkyl, 2-aminoethyl, 3-amino-n-propyl, 2-methylaminoethyl, 3-methylamino-n-propyl, 2-dimethylaminoethyl, 3-dimethylamino-n-propyl, 2-amino-2-carboxyethyl, 3-amino-3-carboxy-n-propyl, 2-trimethylammonioethyl, 2-triethylammonioethyl, 3-trimethylammonio-n-propyl, 3-triethylammonio-n-propyl, 2-hydroxyethyl, 2,3-dihydroxypropyl, 2-methoxyethyl, 3-methoxy-n-propyl, 2,3-ethylenedioxypropyl, 2,3-(2,2-propylene)dioxypropyl, 2-chloro- or 2-bromoethyl, 2- or 3-chloro-n-propyl or 2- or 3-bromo-n-propyl, or a carbohydrate radical of 5 to 12 carbon atoms in an aqueous phase which is raised to a pH-value at least 11 or (b) a homogeneous layer of a phospholipid of the formula A wherein m is 0 or 1, one of $R_1$ and $R_2$ is hydrogen, hydroxy or $C_1$-$C_4$-alkyl, and the other is alkyl, alkenyl, alkoxy or alkenyloxy, each of 10 to 20 carbon atoms, or is acyloxy of 10 to 50 carbon atoms, $R_3$ is hydrogen, and $R_4$ is lower alkyl which is substituted by an ammonio group and an additional phospholipid of the formula A wherein each of $R_1$ and $R_2$ independently of the other are alkyl, alkenyl, alkoxy or alkenyloxy, each of 10–20 carbon atoms, or is acyloxy of 10–50 carbon atoms, $R_3$ is hydrogen or $C_1$-$C_4$-alkyl and $R_4$ is $C_1$-$C_7$-alkyl, carboxy-lower alkyl, 2-aminoethyl, 3-amino-n-propyl, 2-methylaminoethyl, 3-methylamino-n-propyl 2-dimethylaminoethyl, 3-dimethylamino-n-propyl, 2-amino-2-carboxyethyl, 3-amino-3-carboxy-n-propyl, 2-trimethylammonioethyl, 2-triethylammonioethyl, 3-trimethylammonio-n-propyl, 3-triethylammonio-n-propyl, 2-hydroxyethyl, 2,3-dihydroxypropyl, 2methoxyethyl, 3-methoxy-n-propyl, 2,3-ethylene-dioxypropyl, 2,3-(2,2-propylene) dioxypropyl, 2-chloro- or 2-bromoethyl, 2- or 3-chloro-n-propyl or 2- or 3-bromo-n-propyl, or a carbohydrate radical of 5 to 12 carbon atoms; or of a phospholipid of the formula A, wherein m is 0 or 1, each of $R_1$ and $R_2$ independently of the other is alkyl, alkenyl or alkenyloxy, each of 10 to 20 carbon atoms, or is acyloxy of 10 to 50 carbon atoms, $R_3$ is hydrogen, and $R_4$ is lower alkyl which is substituted by an ammonio-lower alkylammonio group and an additional phospholipid of the formula A wherein each of $R_1$ and $R_2$ independently of the other are alkyl, alkenyl, alkoxy or alkenoxy, each of 10–20 carbon atoms, or is acyloxy of 10–50 carbon atoms, $R_3$ is hydrogen or $C_1$-$C_4$-alkyl and $R_4$ is $C_1$-$C_7$-alkyl, carboxy-lower alkyl, 2-aminoethyl, 3-amino-n-propyl, 2-methylaminoethyl, 3-methylamino-n-propyl, 2-dimethylaminoethyl, 3-dimethylamino-n-propyl, 2-amino-2-carboxyethyl, 3-amino-3-carboxy-n-propyl, 2-trimethylammonioethyl, 2-triethylammonioethyl, 3-trimethylammonio-n-propyl, 3-triethylammonio-n-propyl, 2-hydroxyethyl, 2,3-dihydroxypropyl, 2-methoxyethyl, 3-methoxy-n-propyl, 2,3-ethylenedioxypropyl, 2,3-(2,2-propylene)dioxypropyl, 2-chloro- or 2-bromoethyl, 2- or 3-chloro-n-propyl or 2- or 3-bromo-n-propyhl, or a carbohydrate radical of 5 to 12 carbon atoms, in an aqueous phase which is lowered to a pH-value of about or less than about 1 and the aqueous phase is neutralized with a physiologically acceptable acid or base and the unilamellar liposomes obtained are separated from multilamellar liposomes.

2. A process according to claim 1, wherein the aqueous dispersion contains egg phosphatidic acid, or egg phosphatidic acid and egg lecithin.

3. A process according to claim 1, wherein the aqueous dispersion contains egg phosphatidic acid, egg lecithin or beef brain phosphatidylserine.

4. A process according to claim 1, wherein the aqueous dispersion contains asolectin.

5. A process according to claim 1, wherein the aqueous dispersion contains egg phosphatidic acid, egg lecithin and cholesterol.

6. A process according to claim 1, wherein the aqueous dispersion contains lysolecithin and egg lecithin.

7. A process according to claim 1, wherein the aqueous dispersion contains natural lysophosphatidylserine and egg lecithin.

8. A process according to claim 1, wherein a homogeneous layer of the lipids as specified under process (a) is dispersed and the pH value is subsequently raised to about 12.

9. A process according to claim 8, wherein the pH value is raised by the addition of dilute aqueous sodium hydroxide solution or dilute aqueous potassium hydroxide solution.

10. A process according to claim 8, wherein a homogeneous layer of the lipids as specified under process (a) is dispersed in an aqueous phase having a pH value higher than 7.

11. A process according to claim 1, wherein a homogeneous layer of the lipids as specified under process (a) is dispersed in dilute aqueous sodium hydroxide or potassium hydroxide solution.

12. A process according to claim 1, wherein a homogeneous layer of the lipids as specified under process (b) is dispersed in an aqueous phase having a pH of about 1.

13. A process according to claim 1, wherein the aqueous phase is subsequently neutralised by the addition of a physiologically acceptable acid, base or buffer solution having a pH of 7 to 8.

14. A process according to claim 13, wherein the aqueous phase is neutralised by the addition of a physiologically acceptable acid or buffer solution having a pH of 7 to 8.

15. A process according to claim 14, wherein the aqueous phase is neutralised with hydrochloric acid.

16. A process according to claim 1, characterized in that a lipid of the formula A, wherein m is 1, $R_1$ is alkyl, $R_2$ is hydrogen or hydroxy, $R_3$ is hydrogen or lower alkyl, and $R_4$ is hydrogen, $C_1$-$C_7$-alkyl, a carbohydrate radical of 5 to 12 carbon atoms, or a steroid radical, and an additional lipid of the formula A, wherein $R_1$ and $R_2$ are acyloxy, $R_3$ is hydrogen, and $R_4$ is 2-trimethylammonioethyl, 2-aminoethyl, 2-amino-2-carboxyethyl, 3-amino-3-carboxy-n-propyl, or a carbohydrate radical of 5 to 12 carbon atoms are dispersed.

17. A process according to claim 1, characterized in that a lipid of formula A, wherein m is 1, $R_1$ is n-dodecyl (lauryl), n-tetradecyl (myristyl), n-hexadecyl (cetyl), n-octadecyl (stearyl), n-dodecyloxy (lauryloxy), n-tetradecyloxy (myristyloxy), n-hexadecyloxy (cetyloxy), n-octadecyloxy (stearyloxy), lauroyloxy, myristoyloxy, 2-hydroxyethyl, 2,3-ethylenedioxypropyl, 2,3-(2,2-propylene)dioxypropyl, or palmitoyloxy or stearoyloxy, $R_2$ is hydrogen or hydroxy, $R_3$ is hydrogen or methyl, and $R_4$ is hydrogen, methyl, ethyl, 2-amino-2-carboxyethyl, 3-amino-3-carboxy-n-propyl, 2-hydroxyethyl, 2,3-dihydroxypropyl, 2,3-ethylenedioxypropyl, 2,3-(2,2-propylene)dioxypropyl, 2-chloroethyl, 2-bromoethyl, or the inositol radical and an additonal lipid of formula A wherein $R_1$ and $R_2$ are lauroyloxy, myristoyloxy, palmitoyloxy, or stearoyloxy, $R_3$ is hydrogen and $R_4$ is trimethylammonioethyl or 2-aminoethyl, are dispersed.

18. A process according to claim 1, characterized in that natural lysophosphatidic acid, a synthetic lysophosphatidic acid, beef brain lysophosphatidylserine, synthetic lysophosphatidylserine, lysophosphatidylglycerol, lysophosphatidylinositol, and additionally natural lecithin, synthetic lecithin containing identical acyloxy groups, synthetic lecithin containing different acyloxy groups, or natural cephalin or synthetic cephalin containing different acyloxy groups are dispersed.

19. A process according to claim 1, characterized in that egg lysophosphatidic acid, 1-lauroyllysophosphatidic acid, 1-myristoyllysophosphatidic acid, 1-palmitoyllysophosphatidic acid, 1-myristoyllysophosphatidylserine, 1-palmitoyllysophosphatidylserine, and additionally egg lecithin 1-palmitoyl-2-oleoyllecithin, or 1-palmitoyl-2-oleoylcephalin are dispersed.

20. A process according to claim 1, characterized in that a lipid of the formula A, wherein $R_1$ and $R_2$ are acyloxy and $R_3$ and $R_4$ are hydrogen, and optionally an additional lipid of the formula A, wherein $R_1$ and $R_2$ are acyloxy, $R_3$ is hydrogen, and $R_4$ is 2-trimethylammonioethyl, 2-aminoethyl, 2-amino-2-carboxyethyl, 3-amino-3-carboxy-n-propyl, or a carbohydrate radical of 5 to 12 carbon atoms, are dispersed.

21. A process according to claim 1, characterized in that a lipid of formula A, wherein $R_1$ and $R_2$ are lauroyloxy, myristoyloxy, palmitoyloxy, or stearoyloxy, $R_3$ and $R_4$ are hydrogen and optionally an additional lipid of the formula A, wherein $R_1$ and $R_2$ are lauroyloxy, myristoyloxy, palmitoyloxy, or stearoyloxy, $R_3$ is hydrogen and $R_4$ is 2-trimethylammonioethyl, 2-aminoethyl, 2-amino-2-carboxyethyl, 3-amino-3-carboxy-n-propyl or the inositol radical, are dispersed.

22. A process according to claim 1, characterized in that natural phosphatidic acid or synthetic phosphatidic acid, and optionally natural lecithin, synthetic lecithin containing identical acyloxy groups, synthetic lecithin containing different acyloxy groups, natural cephalin, synthetic cephalin containing different acyloxy groups, natural phosphatidylserine, or synthetic phosphatidylserine are dispersed.

23. A process according to claim 1, characterized in that egg phosphatidic acid, dilauroyl-, dimyristoyl-, diphalmitoyl-, or 1-palmitoyl-2-oleoylphosphatidic acid and optionally egg lecithin, dimyristoyl- or dipalmitoyllecithin, 1-palmitoyl-2-oleoyllecithin, beef brain phosphatidylserine or dipalmitoylphosphatidylserine are dispersed.

24. A process according to claim 1, wherein the aqueous phase is neutralised by addition of a physiologically acceptable base.

* * * * *